United States Patent
Lanci et al.

(10) Patent No.: US 10,287,230 B2
(45) Date of Patent: May 14, 2019

(54) SELECTIVE AEROBIC OXIDATION OF DIMETHYLBIPHENYLS

(71) Applicant: ExxonMobil Research and Engineering Company, Annandale, NJ (US)

(72) Inventors: Michael P. Lanci, Flemington, NJ (US); Joshua W. Allen, Branchburg, NJ (US); Jarid M. Metz, Doylestown, PA (US); Victor DeFlorio, Newton, NJ (US); Jihad M. Dakka, Whitehouse Station, NJ (US); Bryan A. Patel, Jersey City, NJ (US); Michael Salciccioli, Houston, TX (US); Michael W. Weber, Houston, TX (US); Stephen Zushma, Clinton, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/829,008

(22) Filed: Dec. 1, 2017

(65) Prior Publication Data

US 2018/0179141 A1 Jun. 28, 2018

Related U.S. Application Data

(60) Provisional application No. 62/437,823, filed on Dec. 22, 2016, provisional application No. 62/437,892, filed on Dec. 22, 2016.

(51) Int. Cl.
| | |
|---|---|
| *C07C 57/30* | (2006.01) |
| *C07C 67/05* | (2006.01) |
| *C07C 25/13* | (2006.01) |
| *C07C 47/23* | (2006.01) |
| *B01J 31/04* | (2006.01) |
| *C07C 51/265* | (2006.01) |
| *C07C 51/16* | (2006.01) |
| *C07C 67/08* | (2006.01) |

(52) U.S. Cl.
CPC ............ *C07C 57/30* (2013.01); *B01J 31/04* (2013.01); *C07C 25/13* (2013.01); *C07C 47/23* (2013.01); *C07C 51/16* (2013.01); *C07C 51/265* (2013.01); *C07C 67/05* (2013.01); *C07C 67/08* (2013.01)

(58) Field of Classification Search
CPC ....... C07C 67/08; C07C 51/16; C07C 51/265; C07C 63/331; C07C 63/333; C07C 25/13; C07C 47/23; C07C 57/30; C07C 67/05; B01J 31/04

See application file for complete search history.

(56) References Cited

U.S. PATENT DOCUMENTS

| | | | |
|---|---|---|---|
| 2,723,994 A * | 11/1955 | Haefele | C07C 51/265 |
| | | | 562/412 |
| 3,660,477 A | 5/1972 | Otterbach et al. | |
| 5,763,649 A | 6/1998 | Fukuhara | |
| 6,274,756 B1 | 8/2001 | Caers et al. | |
| 6,730,625 B1 | 5/2004 | Chang et al. | |
| 7,855,305 B2 | 12/2010 | Parker et al. | |
| 9,328,053 B2 | 5/2016 | Bai et al. | |
| 9,580,572 B2 | 2/2017 | Dakka et al. | |
| 9,663,417 B2 | 5/2017 | Dakka et al. | |
| 2014/0212666 A1 | 7/2014 | Dakka et al. | |
| 2014/0315021 A1 | 10/2014 | Naert et al. | |
| 2015/0080546 A1* | 3/2015 | Dakka | C07C 51/265 |
| | | | 528/305 |
| 2015/0099897 A1 | 4/2015 | Buchbinder et al. | |
| 2015/0361027 A1 | 12/2015 | Dakka et al. | |

FOREIGN PATENT DOCUMENTS

| | | | |
|---|---|---|---|
| JP | 07025817 | * | 1/1995 |
| WO | 2000015597 A1 | | 3/2000 |
| WO | 200575403 A1 | | 8/2005 |
| WO | 2014117076 A1 | | 7/2014 |
| WO | 2015112252 A1 | | 7/2015 |
| WO | 2015191281 A1 | | 12/2015 |

OTHER PUBLICATIONS

JP07025817 translation 1995 (Year: 1995).*
Tris(acetoacetonyl)cobalt 2015 (Year: 2015).*
Libre Texts (published Aug. 2016) (Year: 2016).*
Byron et al., "Effects of 3'- and 4'-substituents on the ionization constants of biphenyl-4-carboxylic acid and 4-aminobiphenyl", J. Chem. Soc. C, 1966, vol. 9, pp. 831-836.
Godwin, "Plasticizers", Applied Polymer Science 21st Century, ed. Craver and Carraher, Elsevier (2000), pp. 157-175.

* cited by examiner

*Primary Examiner* — Yevgeny Valenrod
*Assistant Examiner* — Blaine G Doletski
(74) *Attorney, Agent, or Firm* — Robert A. Migliorini; Kristina Okafor

(57) ABSTRACT

A process for selective oxidation of dimethyl-1,1'-biphenyl(s) to form methyl-1,1'-biphenyl mono-carboxylic acid(s), which can be esterified to form plasticizers, comprising contacting a solution of dimethyl-1,1'-biphenyl(s) in acetic acid in the presence of an oxidation catalyst and air under time and temperature conditions sufficient to oxidize the dimethyl-1,1'-biphenyl(s) into one or more methyl-1,1'-biphenyl mono-carboxylic acid(s) products, conducting at least one of (i) adding an antisolvent, or (ii) optimizing a total conversion of dimethyl-1,1'-biphenyl(s) by oxidation based upon a molar ratio of dimethyl-1,1'-biphenyl isomers, or (iii) precipitating the methyl-1,1'-biphenyl mono-carboxylic acid(s) products by lowering the temperature, or (iv) decreasing the oxidation reaction temperature to enhance conversion of aldehydes over methyl functional groups, so as to limit over-oxidation of the dimethyl-1,1'-biphenyl(s), wherein the oxidation reaction is conducted in the absence of bromide-containing catalysts.

40 Claims, 7 Drawing Sheets

SELECTIVE AEROBIC OXIDATION OF DIMETHYLBIPHENYLS

CROSS-REFERENCE TO RELATED APPLICATIONS

This application claims the benefit of U.S. Provisional Application No. 62/437,823, filed on Dec. 22, 2016, the entire contents of which are incorporated herein by reference.

This application also claims the benefit of related U.S. Provisional Application No. 62/437,892, filed on Dec. 22, 2016, the entire contents of which are incorporated herein by reference.

FIELD

Disclosed are processes for improving selective oxidation of dimethyl biphenyls in the presence of air by modifying various parameters to improve reaction rate and favor formation of methylbiphenyl mono-carboxylic acids.

BACKGROUND

Plasticizers are incorporated into a resin (usually a plastic or elastomer) to increase the flexibility, workability, or dispensability of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for 85% worldwide of PVC plasticizer usage in 2002.

It would be advantageous to develop a new generation of plasticizers with improved performance compared to phthalate esters.

SUMMARY

Presented herein is a process for selective oxidation of dimethyl-1,1'-biphenyl(s) to form methyl-1,1'-biphenyl mono-carboxylic acid(s), comprising contacting a solution of dimethyl-1,1'-biphenyl(s) in acetic acid in the presence of an oxidation catalyst and air under time and temperature conditions sufficient to oxidize the dimethyl-1,1'-biphenyl(s) into one or more methyl-1,1'-biphenyl mono-carboxylic acid(s) products, conducting at least one of (i) adding an antisolvent, or (ii) optimizing a total conversion of dimethyl-1,1'-biphenyl(s) by oxidation based upon a molar ratio of dimethyl-1,1'-biphenyl isomers, or (iii) precipitating the methyl-1,1'-biphenyl mono-carboxylic acid(s) products by lowering the temperature, or (iv) decreasing the oxidation reaction temperature to enhance conversion of aldehydes over methyl functional groups, so as to limit over-oxidation of the dimethyl-1,1'-biphenyl(s), wherein the oxidation reaction is conducted in the absence of bromide-containing catalysts.

Advantageously, the catalyst is Mn(II) acetate or Co(II) acetate or combinations of Co(II) acetate and other metal acetate catalysts.

Conveniently, according to the process the selectivity for formation of methyl-1,1'-biphenyl mono-carboxylic acids is enhanced relative to the formation of other 1,1'-biphenyl oxygenates.

In one form, the process comprises adding water as the antisolvent.

In another form the dimethyl-1,1'-biphenyl is provided in a mixture of dimethylbiphenyl isomers.

In another form, the process further comprises separating 2,3'- and 2,4'-isomers of dimethylbiphenyl from 3,3'-dimethylbiphenyl, 3,4'-dimethylbiphenyl and 4,4'-dimethylbiphenyl by distillation, and dissolving the 3,3'-, 3,4'- and 4,4'-isomers of dimethylbiphenyl in the acetic acid to form the solution.

Additionally, the process further comprises limiting the total conversion to 55-70%/o when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates; or limiting the total conversion to 45-55% when the 3,3'-isomers of dimethylbiphenyl comprise between 10 and 30 wt % in the feed, so as to increase the overall yield of methyl-1,1'-biphenyl mono-carboxylic acids relative to other 1,1'-biphenyl oxygenates; or limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

In another form, precipitation of the methyl-1,1'-biphenyl mono-carboxylic acid(s) products is achieved by removing solvent.

Alternatively, precipitation of the methyl-1,1'-biphenyl mono-carboxylic acid(s) products is achieved by optimizing the oxidation reaction temperature and solute concentrations of the methyl-1,1'-biphenyl mono-carboxylic acid(s), to cause precipitation of the methyl-1,1'-biphenyl mono-carboxylic acid(s) products prior to over-oxidation, such as wherein the oxidation reaction temperature is reduced from an oxidation initiation temperature to from about 40° C. to less than about 60° C., or even wherein the oxidation reaction temperature is about 50° C., and the solute concentration of methyl-1,1'-biphenyl mono-carboxylic acid(s) products is above about 2 wt %, such as wherein the solute concentration of methyl-1,1'-biphenyl mono-carboxylic acid(s) products is from about 2 wt % to about 10 wt %.

In another form, the oxidation reaction temperature is controlled to be from about 100° C. to about 150° C., or even from about 110° C. to about 150° C., or even from about 110° C. to about 130° C.

In another form, the oxidation reaction temperature starts at greater than or equal to about 130° C. and is reduced to about 100° C. after reaction initiation.

Advantageously, the catalyst is Co(II) acetate and further comprising adding one of Mn(II) acetate, Ni(II) acetate, Zn(II) acetate, Zr(IV) acetate, Fe(III) acetate or combinations thereof as the additional metal acetate catalyst, which catalysts can be present in concentrations in the solution from about 7.6 mM (450 ppm) to about 100 mM (6000 ppm), or from about 23 mM (1350 ppm) to about 100 mM (6000 ppm).

In another form, the process further comprises adding Co(III)(acetylacetonate)$_3$, benzaldehyde, acetaldehyde or biphenyl-aldehydes as an initiator.

In another form, the process further comprises separation of the methyl-1,1'-biphenyl mono-carboxylic acid(s) products from under-oxidized intermediates and over-oxidized products, and recycling the under-oxidized intermediates to the oxidation process.

Advantageously, the methyl-1,1'-biphenyl mono-carboxylic acids products formed are one or more of 3,3'-methyl-1,1'-biphenyl mono-carboxylic acid, 3,4'-methyl-1,1'-biphenyl mono-carboxylic acid, 4,3'-methyl-1,1'-biphenyl mono-carboxylic acid, and 4,4'-methyl-1,1'-biphenyl mono-carboxylic acid.

Additionally presented herein is a process for forming methylbiphenyl mono-esters comprising selectively oxidizing dimethyl-1,1'-biphenyl(s) to form methyl-1,1'-biphenyl mono-carboxylic acid(s), comprising contacting a solution of dimethyl-1,1'-biphenyl(s) in acetic acid in the presence of an oxidation catalyst and air under time and temperature conditions sufficient to oxidize the dimethyl-1,1'-biphenyl(s) into one or more methyl-1,1'-biphenyl mono-carboxylic acid(s) products, conducting at least one of (i) adding an antisolvent, or (ii) optimizing a total conversion of dimethyl-1,1'-biphenyl(s) by oxidation based upon a molar ratio of dimethyl-1,1'-biphenyl isomers, or (iii) precipitating the methyl-1,1'-biphenyl mono-carboxylic acid(s) products by lowering the temperature, or (iv) decreasing the oxidation reaction temperature to enhance conversion of aldehydes over methyl functional groups, so as to limit over-oxidation of the dimethyl-1,1'-biphenyl(s), wherein the oxidation reaction is conducted in the absence of bromide-containing catalysts, and further reacting the methyl-1,1'-biphenyl mono-carboxylic acid(s) products with $C_4$ to $C_{13}$ alcohols under esterification conditions.

Advantageously, the catalyst is Mn(II) acetate or Co(II) acetate or combinations of Co(II) acetate and other metal acetate catalysts.

Conveniently, according to the process the selectivity for formation of methyl-1,1'-biphenyl mono-carboxylic acids is enhanced relative to the formation of other 1,1'-biphenyl oxygenates.

In one form, the process comprises adding water as the antisolvent.

In another form the dimethyl-1,1'-biphenyl is provided in a mixture of dimethylbiphenyl isomers.

In another form, the process further comprises separating 2,3'- and 2,4'-isomers of dimethylbiphenyl from 3,3'-dimethylbiphenyl, 3,4'-dimethylbiphenyl and 4,4'-dimethylbiphenyl by distillation, and dissolving the 3,3'-, 3,4'- and 4,4'-isomers of dimethylbiphenyl in the acetic acid to form the solution.

Additionally, the process further comprises limiting the total conversion to 55-70% when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates; or limiting the total conversion to 45-55% when the 3,3'-isomers of dimethylbiphenyl comprise between 10 and 30 wt % in the feed, so as to increase the overall yield of methyl-1,1'-biphenyl mono-carboxylic acids relative to other 1,1'-biphenyl oxygenates; or limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

In another form, precipitation of the methyl-1,1'-biphenyl mono-carboxylic acid(s) products is achieved by removing solvent.

Alternatively, precipitation of the methyl-1,1'-biphenyl mono-carboxylic acid(s) products is achieved by optimizing the oxidation reaction temperature and solute concentrations of the methyl-1,1'-biphenyl mono-carboxylic acid(s), to cause precipitation of the methyl-1,1'-biphenyl mono-carboxylic acid(s) products prior to over-oxidation, such as wherein the oxidation reaction temperature is reduced from an oxidation initiation temperature to from about 40° C. to less than about 60° C., or even wherein the oxidation reaction temperature is about 50° C., and the solute concentration of methyl-1,1'-biphenyl mono-carboxylic acid(s) products is above about 2 wt %, such as wherein the solute concentration of methyl-1,1'-biphenyl mono-carboxylic acid(s) products is from about 2 wt % to about 10 wt %.

In another form, the oxidation reaction temperature is controlled to be from about 100° C. to about 150° C., or even from about 110° C. to about 150° C., or even from about 110° C. to about 130° C.

In another form, the oxidation reaction temperature starts at greater than or equal to about 130° C. and is reduced to about 100° C. after reaction initiation.

Advantageously, the catalyst is Co(II) acetate and further comprising adding one of Mn(II) acetate, Ni(II) acetate, Zn(II) acetate, Zr(IV) acetate, Fe(II) acetate or combinations thereof as the additional metal acetate catalyst, which catalysts can be present in concentrations in the solution from about 7.6 mM (450 ppm) to about 100 mM (6000 ppm), or from about 23 mM (1350 ppm) to about 100 mM (6000 ppm).

In another form, the process further comprises adding Co(III)(acetylacetonate)$_3$, benzaldehyde, acetaldehyde or biphenyl-aldehydes as an initiator.

In another form, the process further comprises separation of the methyl-1,1'-biphenyl mono-carboxylic acid(s) products from under-oxidized intermediates and over-oxidized products, and recycling the under-oxidized intermediates to the oxidation process.

Advantageously, the methyl-1,1'-biphenyl mono-carboxylic acids products formed are one or more of 3,3'-methyl-1,1'-biphenyl mono-carboxylic acid, 3,4'-methyl-1,1'-biphenyl mono-carboxylic acid, 4,3'-methyl-1,1'-biphenyl mono-carboxylic acid, and 4,4'-methyl-1,1'-biphenyl mono-carboxylic acid.

Advantageously, the alcohols are OXO-alcohols.

BRIEF DESCRIPTION OF THE DRAWINGS

The present disclosure is susceptible to various modifications and alternative forms, specific exemplary implementations thereof have been shown in the drawings and are herein described in detail. It should be understood, however, that the description herein of specific exemplary implementations is not intended to limit the disclosure to the particular forms disclosed herein.

DETAILED DESCRIPTION

Figure 1:
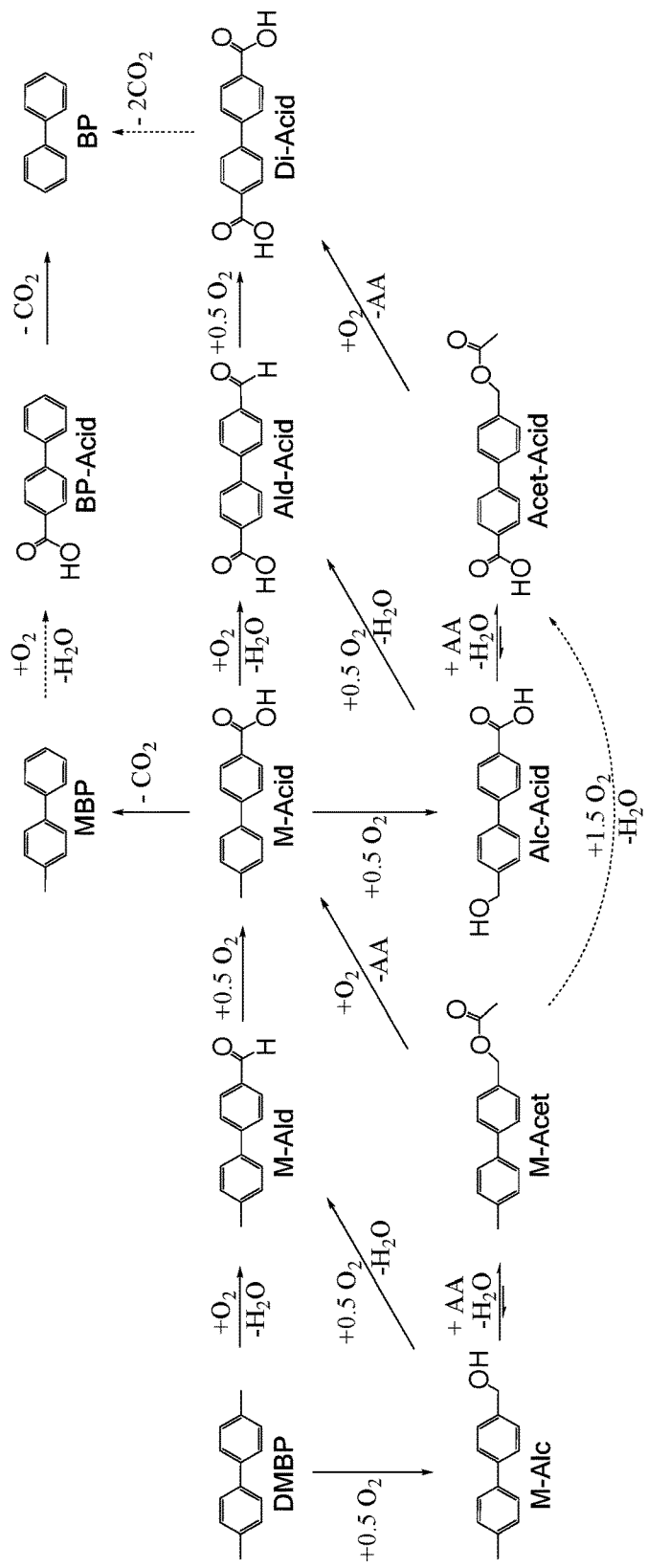
FIG. 1 shows a number of possible reaction pathways for oxidation of 4,4'-DMBP.

There is an increased interest in developing new plasticizers which possess good plasticizer performance characteristics but are still competitive economically. The present disclosure is directed towards OXO-ester plasticizers, that can be made from low cost feeds and employ fewer manufacturing steps in order to meet economic targets.

Definitions

The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

A/an: The articles "a" and "an" as used herein mean one or more when applied to any feature in embodiments and implementations of the present invention described in the specification and claims. The use of "a" and "an" does not limit the meaning to a single feature unless such a limit is specifically stated. The term "a" or "an" entity refers to one or more of that entity. As such, the terms "a" (or "an"), "one or more" and "at least one" can be used interchangeably herein.

About: As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussion below regarding ranges and numerical data. All numerical values within the detailed description and the claims herein are modified by "about" the indicated value And/or: The term "and/or" placed between a first entity and a second entity means one of (1) the first entity, (2) the second entity, and (3) the first entity and the second entity. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements). As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of".

Comprising: In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. Any device or method or system described herein can be comprised of, can consist of, or can consist essentially of any one or more of the described elements.

Ranges: Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and about 200, but also to include individual sizes such as 2, 3, 4, etc. and sub-ranges such as 10 to 50, 20 to 100, etc. Similarly, it should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds). In the figures, like numerals denote like, or similar, structures and/or features; and each of the illustrated structures and/or features may not be discussed in detail herein with reference to the figures. Similarly, each structure and/or feature may not be explicitly labeled in the figures, and any structure and/or feature that is discussed herein with reference to the figures may be utilized with any other structure and/or feature without departing from the scope of the present disclosure.

The term dimethylbiphenyl (DMBP) refers to the starting compound of the presently described processes, which is 4,4'-dimethyl-1,1'-biphenyl having the following chemical structure:

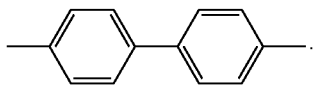

Other suitable starting isomers include 3,3'-dimethyl-1,1'-biphenyl and 3,4'-dimethyl-1,1'-biphenyl, which often occur in mixtures with 4,4'-dimethyl-1,1'-biphenyl. For convenience, the structures below are shown as the 4,4'-isomers, but it will be understood that the 3,3'-, 4,3'- and 3,4'-isomers of these compounds are also covered by the general terminologies.

The term "M-Acid" refers to a mono-carboxylic acid of a DMBP molecule, in particular 4'-methyl-1,1'-biphenyl-4-carboxylic acid, a desired product of the present processes. The chemical structure of methyl-1,1'-biphenyl-carboxylic acid is:

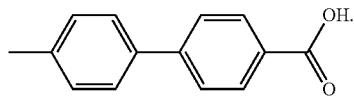

The term "M-Ald" refers to a mono-aldehyde of a DMBP molecule, which has the following chemical structure:

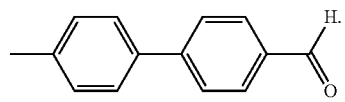

The term "M-Alc" refers to a mono-methlalcohol of a DMBP molecule, which has the following chemical structure:

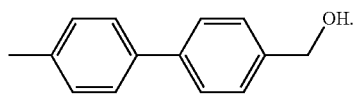

The term "M-Acet" refers to a mono-methylacetate of a DMBP molecule, which has the following chemical structure:

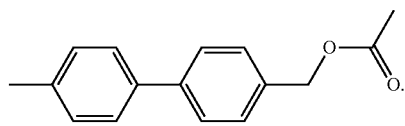 [SMILES: CC(=O)OCc1ccc(-c2ccc(C)cc2)cc1]

The term "Alc-Acid" refers to a biphenyl molecule having a methylalcohol substituent on one ring and an acid substituent on the other ring, which has the following chemical structure:

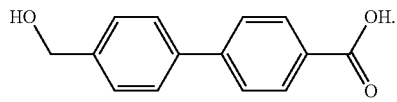

The term "Ald-Acid" refers to a biphenyl molecule having an aldehyde substituent on one ring and an acid substituent on the other ring, which has the following chemical structure:

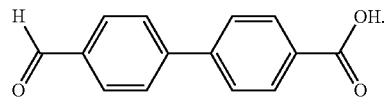

The terms "Di-Acid" or "D-Acid" refers to a biphenyl molecule having carboxylic acid substituents on each ring, which has the following chemical structure.

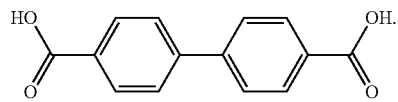

The term "Acet-Acid" refers to a biphenyl molecule having a methylacetate substituent on one ring and an acid substituent on the other ring, which has the following chemical structure:

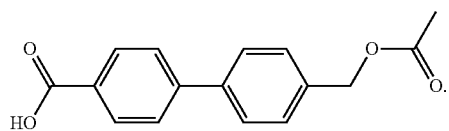

The various biphenyl molecules described above which have oxygen-containing moieties on both phenyl groups are considered to be "over-oxidized" products.

An "OXO-ester" is a compound having at least one functional ester moiety within its structure derived from esterification of either an acid or alcohol compound with an OXO-alcohol or OXO-acid, respectively.

An "OXO-alcohol" is an organic alcohol, or mixture of organic alcohols, which is prepared by hydroformylating an olefin, followed by hydrogenation to form the alcohols. Typically, the olefin is formed by light olefin oligomerization over heterogenous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety. The OXO-alcohols consist of multiple isomers of a given chain length due to the various isomeric olefins obtained in the oligomerization process, in tandem with the multiple isomeric possibilities of the hydroformylation step.

The purpose of the presently disclosed plasticizers is to replace the currently used, phthalate-based plasticizers with an alternative for the global general purpose plasticizer market. One potential route to new products is to use dimethylbiphenyl (DMBP) isomers. The DMBP molecules can be oxidized to produce many molecules. FIG. 1 shows some of the pathways that exist, the dashed arrows representing multiple reaction steps. The methods disclosed herein are specific for improved selectivity to the methyl-1,1'-biphenyl-carboxylic acids (mono-acids). The acid groups can be esterified with OXO-alcohols to produce esters and when the methyl and carboxylic acid groups are on adjacent rings in the 3- or 4-positions, the final esters have excellent plasticizer properties.

The M-Ald, M-Alc and M-Acet molecules are considered to be under-oxidized, but are relatively easily converted to the M-Acid. These under-oxidized molecules can be recycled into the oxidation reaction for conversion to M-Acids. In contrast, the Aid-Acid, Acet-Acid and Di-Acid molecules are considered to be over-oxidized, and coversion back to an M-Acid is more difficult. The processes of the present application explore ways of avoiding over-oxidation products in favor of either under-oxidized products or M-Acids.

There are many homogeneous processes for oxidation of alkylaromatics and most of them involve the full oxidation of all the alkyl groups to carboxylic acids. Some examples include, toluene to benzoic acid, p-xylene to terephthalic acid, m-xylene to isophthalic acid, pseudocumene to trimellitic acid, and 2,6-dimethylnaphthalene to naphthalene-2,6-dicarboxylic acid. These oxidations utilize the cobalt, manganese, and bromide in various ratios in acetic acid. Other processes with ortho-substituted alkyl groups can be oxidized by heterogeneous catalyst to produce anhydrides; for example, o-xylene is oxidized to produce phthalic anhydride over vanadium supported on titanium oxide. The most closely related oxidations to the presently disclosed processes involve methods to retain one of the methyl groups on the aromatic ring. One example is the oxidation of p-xylene to p-toluic acid. Oxidation of p-xylene can be done selectively if desired, utilizing only cobalt as the catalyst. Production of terephthalic acid requires stronger oxidizing. The mixture of cobalt, manganese, and bromide is reported to provide Mn—Br as the strong oxidant in the catalytic cycle.

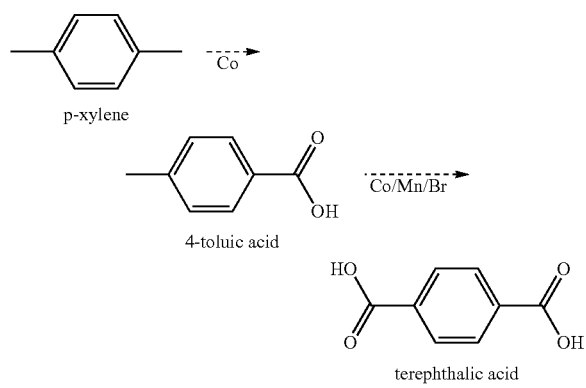

Oxidation of p-xylene to p-toluic acid is fairly easy because the first acid group that forms, deactivates the molecule toward further oxidation. However, the added aromatic ring in DMBP dampens the deactivation, resulting in oxidation of the second methyl group to be fairly close in rate constant to the first.

Figure 2:
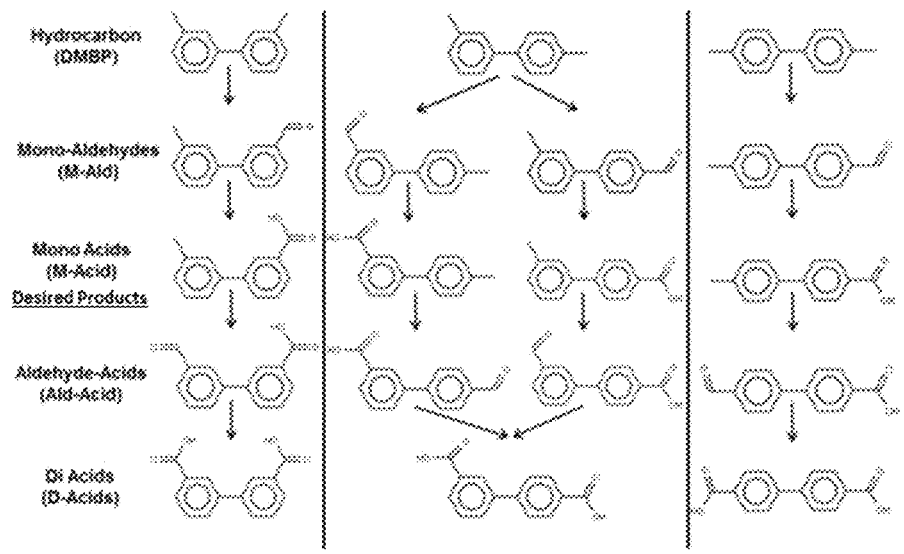
FIG. 2 shows potential oxidation products resulting from oxidation of biphenyl isomers mixtures.

DMBP is produced as a mixture of isomers and while the 2,3'- and 2,4'-isomers can be separated from the 3,3'-, 3,4'-, and 4,4'-DMBP isomers by distillation, additional separation of the latter is very expensive. Therefore, oxidation of a mixture of isomers is desirable, but it has been discovered that the selective oxidation of this mixture is also much more complex than for any of the individual isomers. FIG. 2 illustrates some of the more abundant intermediates and isomers of intermediates of the reaction. The over-oxidized products, such as Ald-Acids and Di-Acids, represent yield loss because no market or feasible method of recovering them as M-Acids currently exists. Stopping the oxidation reaction at the M-Acids with high selectivly for each isomer in a mixture is hampered by the fact that each isomer oxidizes at very different reaction rates. For example, pure 4,4'-DMBP oxidizes approximately 80 times faster than pure 3,3'-DMBP. As shown in Table 1, at 50% conversion of a mixture of the three isomers, the 4,4'-isomer will typically reach 99% conversion before 3,3'-isomer reaches 20% conversion, and this leads to significant yields of unusable over-oxidation products.

TABLE 1

Yields of isomers at 50% conversion total DMBP

| Isomer | M-Ald | M-Acid | Ald-Acid | Di-Acid | % Isomer Conversion |
|---|---|---|---|---|---|
| 3,3'-DMBP | 6.6% | 14.3% | 0.4% | 0.6% | 20.4% |
| 3,4'-DMBP | 17.1% | 57.9% | 1.8% | 1.1% | 83.8% |
| 4,4'-DMBP | 7.2% | 71.5% | 4.1% | 1.6% | 99.7% |

Figure 3:
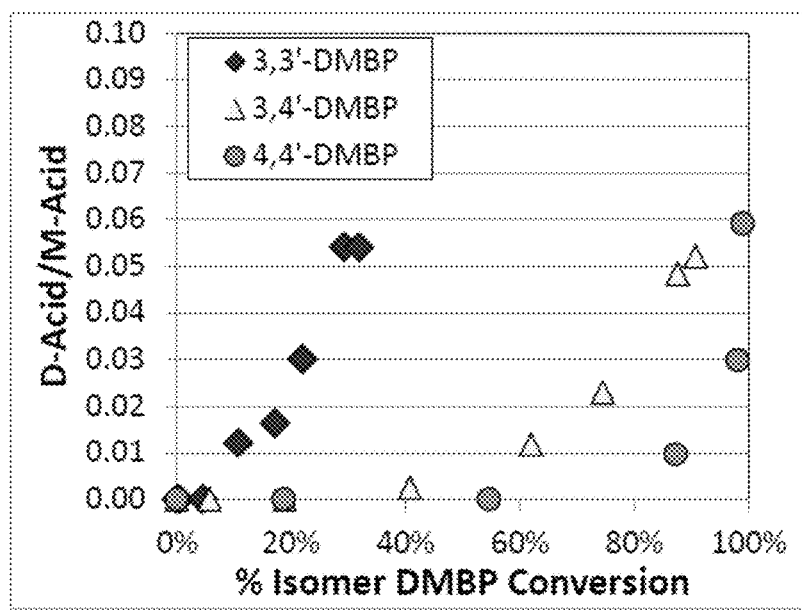
FIG. 3 shows the di-acid to mono-acid ratio as a function of conversion for the three DMBP isomers.

FIG. 3 illustrates the effect that the large difference in rates of reactivity between isomers has on the ratios of Di-Acid and M-Acid for each isomer. The purification of M-Acid is also challenged by having a mixture of isomers. Taking melting point as an indicator of relative solubility (M.P. correlates inversely with solubility), the 3,3'-M-acid (M.P. 133.7° C.) has as very similar melting point as 4,4'-DMBP (M.P. 121.4° C.) and 4,4'-M-aldehyde (M.P. 105.9° C.), whereas the 3,4'-, 4,3'- and 4,4'-M-acids have melting points >185° C. It has been determined that this causes the 3,3'-M-acid isomer to be difficult to precipitate from the product mixture, resulting in 3,3'-M-acid being recycled with the unreacted DMBP to the oxidation reactor where it becomes over-oxidized. The presence of soluble 3,3'-M-acid and other under-oxidized intermediates also enhances the solubility of the 3,4'- and 4,4'-M-acid isomers, pulling them into the recycle stream as well. The net result is a nearly entire yield loss of the 3,3'-isomer and low yields of the 3,4'- and 4,4'-M-acids.

In one form is disclosed a process for selective oxidation of dimethyl-1,1'-biphenyl(s) to form methyl-1,1'-biphenyl mono-carboxylic acid(s), comprising contacting a solution of dimethyl-1,1'-biphenyl(s) in acetic acid in the presence of an oxidation catalyst and air under time and temperature conditions sufficient to oxidize the dimethyl-1,1'-biphenyl(s) into one or more methyl-1,1'-biphenyl mono-carboxylic acid(s) products, by conducting at least one of (i) adding an antisolvent, or (ii) optimizing a total conversion of dimethyl-1,1'-biphenyl(s) by oxidation based upon a molar ratio of dimethyl-1,1'-biphenyl isomers, or (iii) precipitating the methyl-1,1'-biphenyl mono-carboxylic acid(s) products by lowering the temperature, or (iv) decreasing the oxidation reaction temperature to enhance conversion of aldehydes over methyl functional groups, so as to limit over-oxidation of the dimethyl-1,1'-biphenyl(s), wherein the oxidation reaction is conducted in the absence of bromide-containing catalysts. The catalyst is Mn(II) acetate or Co(II) acetate or combinations of Co(II) acetate and other metal acetate catalysts.

When the catalyst is Co(II) acetate, it can optionally include Mn(II) acetate, Ni(II) acetate, Zn(II) acetate, Zr(IV) acetate, Fe(II) acetate or combinations thereof as the additional metal acetate catalyst, which catalysts can be present in concentrations in the solution from about 7.6 mM (450 ppm) to about 100 mM (6000 ppm), or from about 23 mM (1350 ppm) to about 100 mM (6000 ppm). Additionally, initiators such as Co(III)(acetylacetonate)$_3$, benzaldehyde, acetaldehyde or biphenyl-aldehydes can be added.

One method of effecting precipitation is to add an antisolvent to the reaction solution. The antisolvent can be any solvent which acts to decrease the solubility of the M-acids in the reaction solution. For example, a suitable antisolvent in this system is water. Addition of even as much as 10 wt % water has the additional advantage of quenching the oxidation reaction so as to reduce the over-oxidation of the DMBP derivatives, without negatively affecting the oxidation reaction to the mono-oxidized intermediates or products.

Another method of effecting precipitation of the desired M-acid products is by removing solvent, such as by vaporizing the acetic acid solvent, thus reducing the solubility of the M-acid products in the solution.

Figure 8:
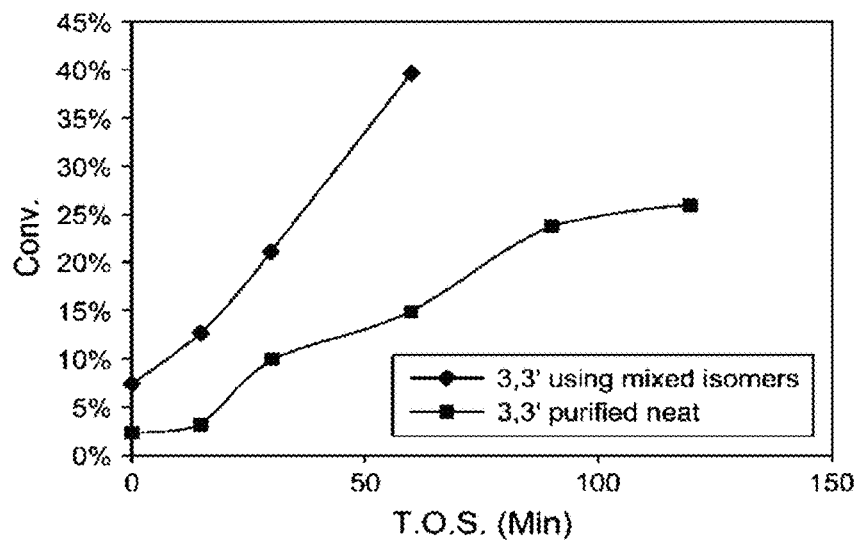
FIG. 8 shows that conversion of 3,3'-DMBP is much slower in the absence of other isomers.

It has also been determined that the relative ratio of DMBP isomers has an effect on the rate of the oxidation reaction. For example, pure 3,3'-DMBP oxidizes quite slowly, while mixtures of DMBP isomers have been demonstrated to oxidize more quickly, and even cause the slowly oxidizing 3,3'-isomer to oxidize more rapidly (FIG. 8). Accordingly, varying the ratio of the more rapidly oxidizing DMBP isomers, such as increasing the concentration of the 4,4'-isomer, results in shorter reaction times for all DMBP isomers.

However, this increase in reaction rate must be balanced against the potential for over-oxidation of the rapidly oxidizing isomers. It has been determined that there are optimum molar ratios of the dimethyl-1,1'-biphenyl isomers, as well as optimum conversion percentages to which the reaction should be driven, in order to maximize M-acid products and minimize over oxidized products. Advantageously, the under oxidized intermediates can be recycled to the oxidation reaction for further oxidation to M-acids.

For example, the total conversion should be limited to 55-70% when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates. Alternatively, the total conversion should be limited to 45-55% when the 3,3'-isomers of dimethylbiphenyl comprise between 10 and 30 wt % in the feed, so as to increase the overall yield of methyl-1,1'-biphenyl mono-carboxylic acids relative to other 1,1'-biphenyl oxygenates, or the total conversion should be limited to 30-45° % when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

Additionally, the oxidation reaction temperature can be optimized to limit over-oxidation products, such as by conducting the oxidation process at temperatures from about from about 100° C. to about 150° C., or even from about 110° C. to about 150° C., or even from about 110° C. to about 130° C. In one form, a two-step temperature profile can be used, wherein the first step is conducting the oxidation reaction at temperatures of greater than about 130° C., up to about 150° C., and the second step is to lower the temperature of the reaction system to less than or equal to about 100° C., to complete mono-oxidation of the products, but to avoid over-oxidation of the products.

Figure 4:
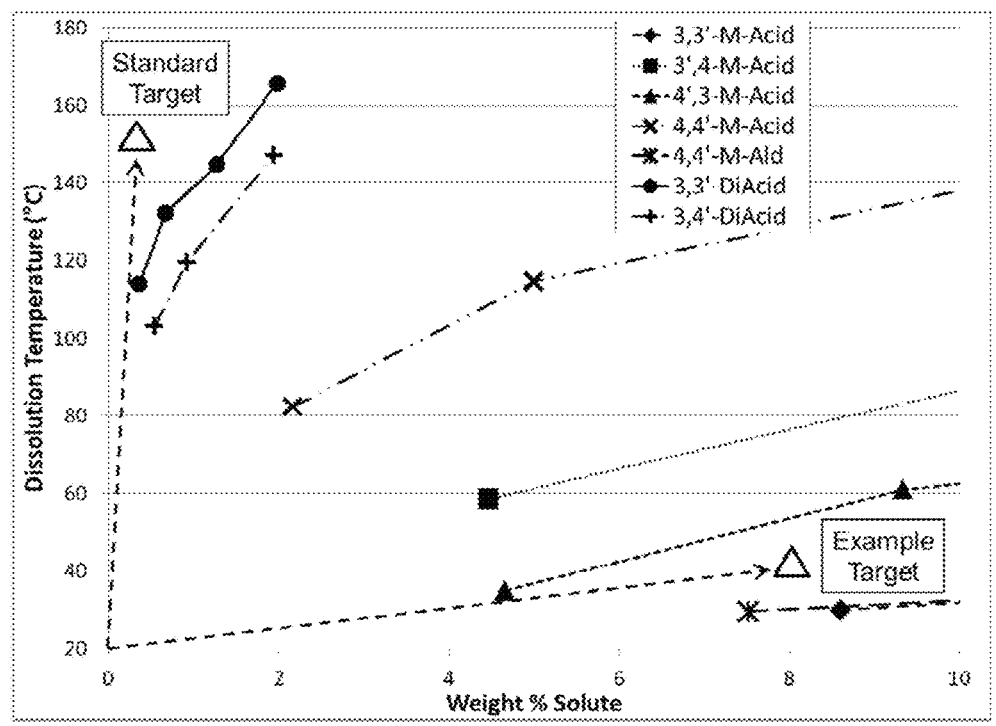
FIG. 4 shows the solubility of various DMBP oxidation products.

One aspect of the presently disclosed process is to select in-reactor conditions to favor precipitation of the methyl-1,1'-biphenyl mono-carboxylic acid(s) products, so as to reduce over-oxidation of the DMBP derivatives. The relative solubility of the oxidation products plays a significant role in the selectivity. Reactor conditions for this process typically range between 100-150° C. and 10-20 wt % DMBP. As shown in FIG. 4, some of the methyl-acid isomers are near to the solubility limit at reaction conditions. In some cases, the reaction conditions can be designed specifically to precipitate the methyl-acid product and remove it from further interaction with the dissolved oxygen species. This approach effectively de-couples the standard oxidation sequence, enabling the ability to quench the oxidation reaction at the desired product and reduce over-oxidation.

For example, precipitation of the methyl-1,1'-biphenyl mono-carboxylic acid(s) products can be achieved by optimizing the oxidation reaction temperature and solute concentrations of the methyl-1,1'-biphenyl mono-carboxylic acid(s), to cause precipitation of the methyl-1,1'-biphenyl mono-carboxylic acid(s) products prior to over-oxidation, such as wherein the oxidation reaction temperature is reduced from an oxidation initiation temperature to from about 40° C. to less than about 60° C., or even wherein the oxidation reaction temperature is reduced to about 50° C., and the solute concentration of methyl-1,1'-biphenyl mono-carboxylic acid(s) products is above about 2 wt %, such as wherein the solute concentration of methyl-1,1'-biphenyl mono-carboxylic acid(s) products is from about 2 wt % to about 10 wt %.

In another form is disclosed a process for forming methylbiphenyl mono-esters comprising selectively oxidizing dimethyl-1,1'-biphenyl(s) to form methyl-1,1'-biphenyl mono-carboxylic acid(s), as described above, comprising contacting a solution of dimethyl-1,1'-biphenyl(s) in acetic acid in the presence of an oxidation catalyst and air under time and temperature conditions sufficient to oxidize the dimethyl-1,1'-biphenyl(s) into one or more methyl-1,1'-biphenyl mono-carboxylic acid(s) products, conducting at least one of (i) adding an antisolvent, or (ii) optimizing a total conversion of dimethyl-1,1'-biphenyl(s) by oxidation based upon a molar ratio of dimethyl-1,1'-biphenyl isomers, or (iii) precipitating the methyl-1,1'-biphenyl mono-carboxylic acid(s) products by lowering the temperature, or (iv) decreasing the oxidation reaction temperature to enhance conversion of aldehydes over methyl functional groups, so as to limit over-oxidation of the dimethyl-1,1'-biphenyl(s), wherein the oxidation reaction is conducted in the absence of bromide-containing catalysts, and further reacting the methyl-1,1'-biphenyl mono-carboxylic acid(s) products with $C_4$ to $C_{13}$ alcohols under esterification conditions. It can be advantageous if the alcohols are OXO-alcohols.

EXAMPLES

Example 1

Oxidation of Mixed DMBP Isomers (2,X'-, 3,X'-, and 4,4'-DMBP)

Figure 5:
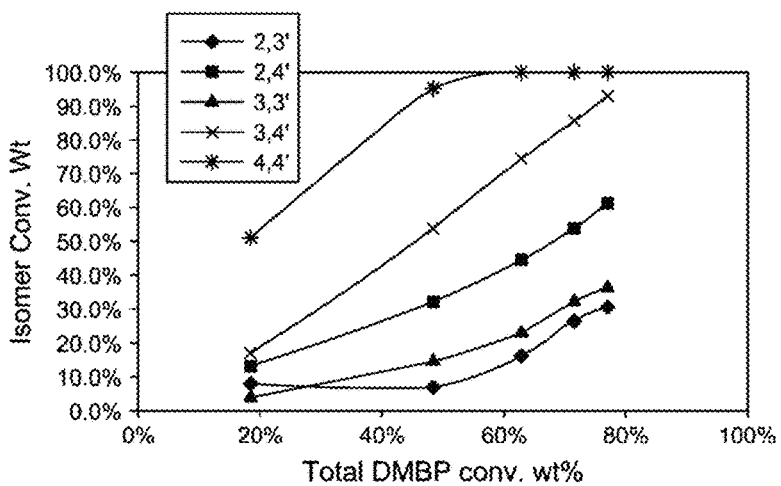
FIG. 5 shows the isomer conversion profile versus total DMBP conversion according to Example 1.

Oxidation was done batchwise. A 300 ml Parr reactor was charged with 30 grams of a dimethylbiphenyl mixed isomer feed (with the following composition 0.6 wt % 2,3'-DMBP, 1.9 wt % 2,4'-DMBP, 29 wt % 3,3'-DMBP, 52.8 wt % 3,4'-DMBP, and 15.7 wt % 4,4'-DMBP), 120 gms acetic acid, and 1500 ppm Co(II) acetate. The reactor was sealed and pressurized to 500 psig (3549 kPa-a) with nitrogen. The reactor was heated to 150° C. with a stir rate of 1200 rpm under 1500 cc/min $N_2$. When the temperature reached 150° C., $N_2$ was switched to air at the same flow rate. During the reaction, liquid samples were taken for GC analysis and the oxygen concentration in the gas effluent was measured. After 2 hours reaction time the air flow was switched to $N_2$, the reactor was cooled to room temperature then depressurized. The oxidation conversion/selectivity profile is shown in FIG. 5. This experiment indicates that mixtures of isomers can be oxidized to mixtures of M-Acids selectively and that the relative reaction rate by ring position is 4>3>2, and by isomer 4,4'>3,4'>2,4'>3,3'>2,3'

Example 2

Oxidation of Individual Isomers (3,3'-, 3,4'-, and 4,4'-DMBP)

Figure 6:
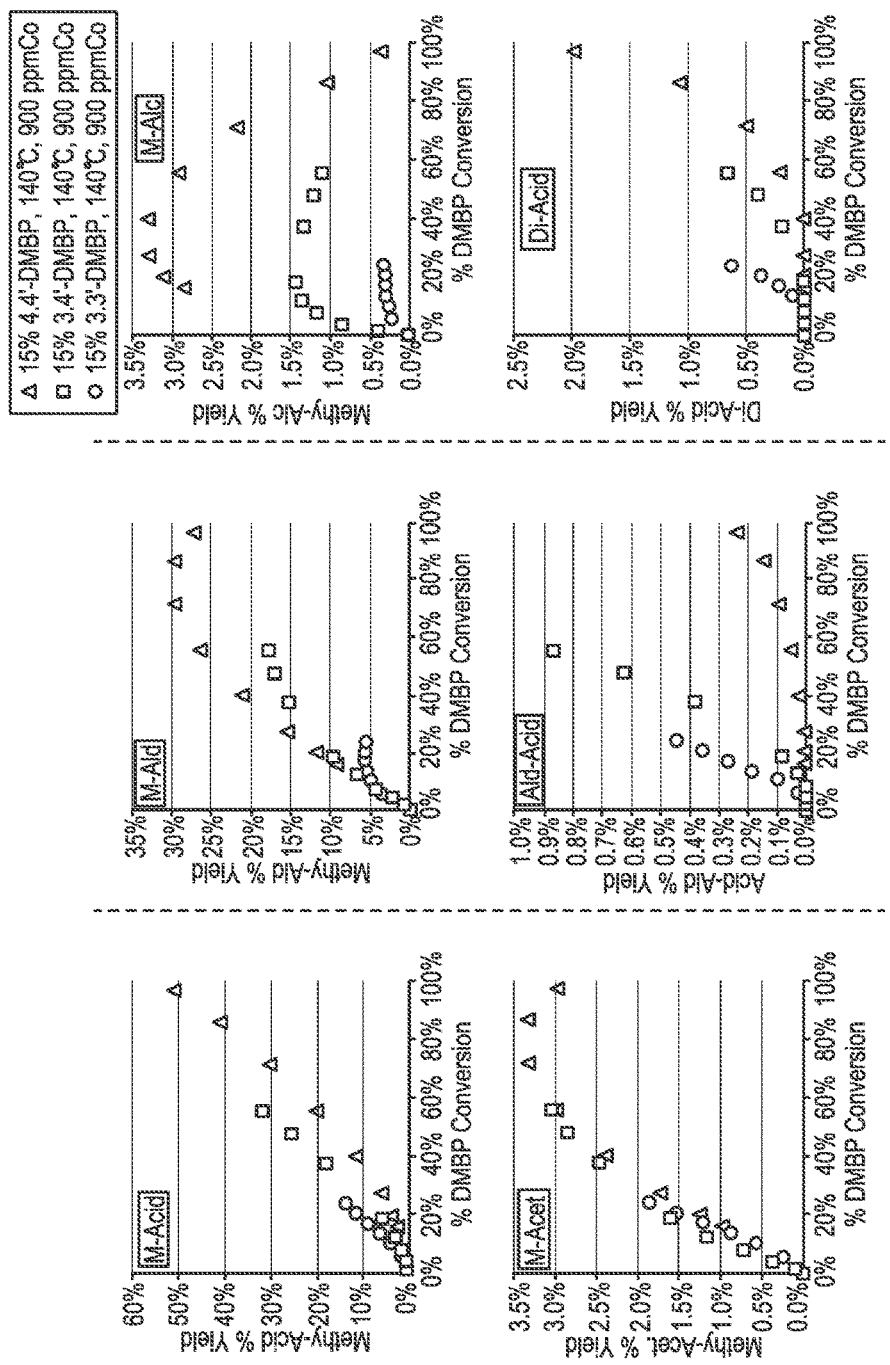
FIG. 6 shows a comparison of yield profiles for oxidation of the pure isomers 3,3'-DMBP, 3,4'-DMBP and 4,4'-DMBP mixtures according to Example 2.

Oxidation was done batchwise with each isomer in a separate reaction. A 300 ml Parr reactor was charged with 26.3 grams of a dimethylbiphenyl (either 3,3'-DMBP, 3,4'-DMBP, or 4,4'-DMBP), 900 ppm Co(II) acetate, and a balance of acetic acid to bring the total weight of the reaction up to 175 g. In the case of 3,3'-DMBP, 1.53 g of benzaldehyde was added to initiate the reaction. The reactor was sealed and pressurized to 500 psig (3549 kPa-a) with nitrogen. The reactor was heated to 140° C. with a stir rate of 1200 rpm under 1500 cc/min $N_2$. When the temperature reached 140° C., $N_2$ was switched to air at the same flow rate. During the reaction, liquid samples were taken for GC analysis and the oxygen concentration in the gas effluent was measured. After the reaction, the air flow was switched to $N_2$, the reactor was cooled to room temperature then depressurized. The oxidation conversion of each individual isomer and corresponding product yields are shown in FIG. 6. This example shows the selectivity of the different isomers to the intermediates, desired products, and over-oxidation products at various conversions. It clearly displays the inherent differences in the relative reactivities of the isomers.

Example 3

Oxidation of Mixed DMBP Isomers (3,3'-, 3,4'-, and 4,4'-DMBP)

Oxidation was done batchwise. A 300 ml Parr reactor was charged with 30 grams of a dimethylbiphenyl mixed isomer feed (with the following composition 25% 3,3'-DMBP, 55% 3,4'-DMBP, and 20% 4,4'-DMBP), 120 gms acetic acid, and 900 ppm Co acetate. The reactor was sealed and pressurized to 500 psig (3549 kPa-a) with nitrogen. The reactor was heated to 150° C. with a stir rate of 1200 rpm under 1500 cc/min $N_2$. When the temperature reached 150° C., $N_2$ was switched to air at the same flow rate. During the reaction, liquid samples were taken for GC analysis and the oxygen concentration in the gas effluent was measured. After the reaction, the air flow was switched to $N_2$, the reactor was cooled to room temperature then depressurized. The results were interpolated to give the yields at 50%, conversion of the total DMBP isomers, shown in Table 2. To limit over-oxidation the process should be run at relatively low conversion of DMBP. The under-oxidized intermediates can be recycled back to the feed.

TABLE 2

| | \multicolumn{7}{c}{Yields at 50% total DMBP conversion} | | | | | | |
|---|---|---|---|---|---|---|---|
| | Me-Alc | Me-Ald | M-Acid | M-Acet | Ald-Acid | Di-Acid | % Conv |
| Total DMBP | 1.0% | 17.6% | 27.0% | 3.4% | 0.2% | 0.5% | 50.6% |
| 3,3'-DMBP | 0.6% | 5.7% | 6.9% | 1.4% | 0.2% | 0.5% | 10.4% |
| 3,4'-DMBP | 1.3% | 19.9% | 26.3% | 3.6% | 0.2% | 0.3% | 52.1% |
| 4,4'-DMBP | 0.8% | 26.3% | 53.9% | 5.3% | 0.2% | 1.3% | 94.0% |

Example 4

Oxidation of Mixed DMBP Isomers (3,3'-, 3,4'-, and 4,4'-DMBP)

Figure 7:
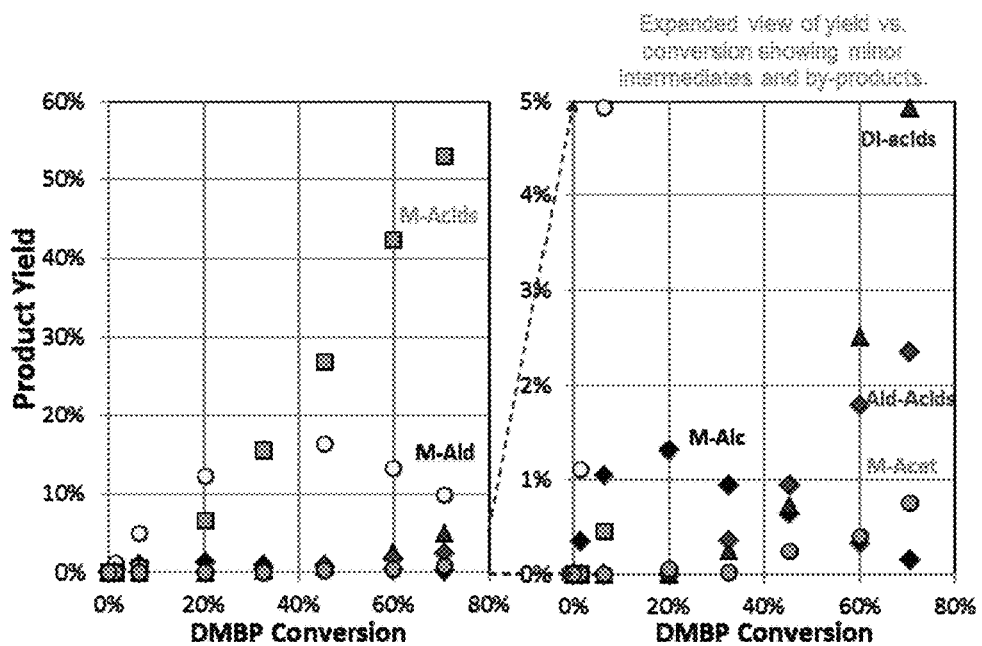
FIG. 7 shows a comparison of yield profiles for oxidation of 3,3'-DMBP, 3,4'-DMBP and 4,4'-DMBP mixtures according to Example 4.

Oxidation was done batchwise. A 300 ml Parr reactor was charged with 30 grams of a dimethylbiphenyl mixed isomer feed (with the following composition 25 wt % 3,3'-DMBP, 55 wt % 3,4'-DMBP, and 20 wt % 4,4'-DMBP), 120 gms acetic acid, and 1500 ppm Co acetate. The reactor was sealed and pressurized to 500 psig (3549 kPa-a) with nitrogen. The reactor was heated to 150° C. with a stir rate of 1200 rpm under 1500 cc/min $N_2$. When the temperature reached 150° C., $N_2$ was switched to air at the same flow rate. During the reaction, liquid samples were taken for GC analysis and the oxygen concentration in the gas effluent was measured. After 2 hours reaction time the air flow was switched to $N_2$, the reactor was cooled to room temperature then depressurized. The oxidation selectivity vs. conversion profile is shown in FIG. 7. To limit over-oxidation the process should be run at relatively low conversion of DMBP. The under-oxidized intermediates can be recycled back to the feed.

Example 5

Figure 9:
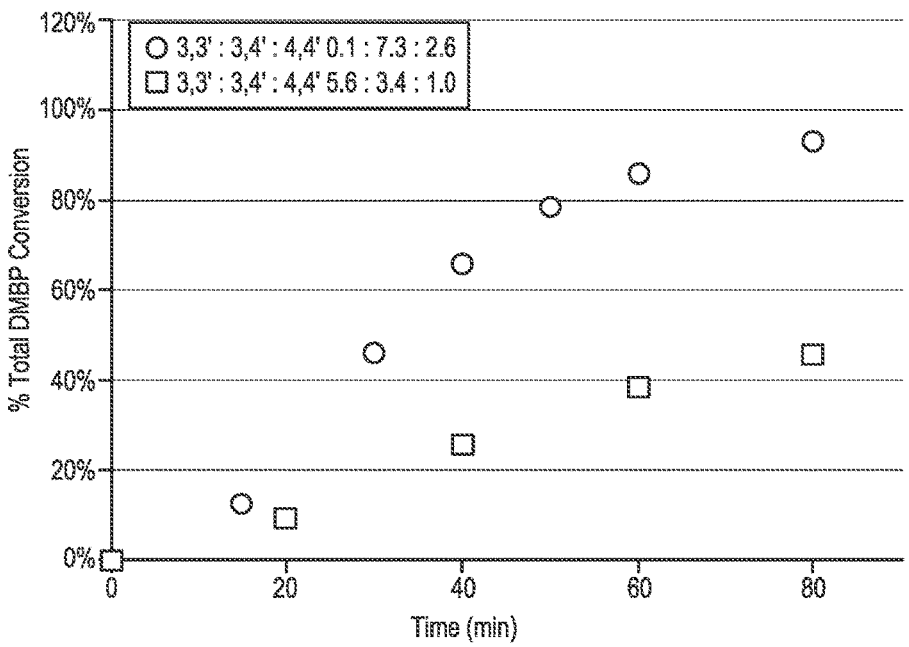
FIG. 9 shows that decreasing the concentration of 3,3'-DMBP relative to the other isomers of DMBP increases the overall reaction rate.

Comparison of Oxidation of DMBP Isomers with Varying Concentrations of 3,3'-DMBP Oxidation of the 3,3'-DMBP isomer is very sluggish in the absence of an initiator. Having a 4,4'-DMBP and/or 3,4'-DMBP in the feed increases the reaction rate, allowing 3,3'-DMBP oxidation to proceed uninhibited. In FIG. 8, oxidation rates of 3,3'-DMBP alone and in the presence of other isomers was compared. The reaction conditions were identical (20 wt % total DMBP, 150° C., and 25 mM Co) except for the DMBP composition being varied from pure 3,3'-DMBP to a mixed ratio of 25:55:20 for 3,3':3,4':4,4'-DMBP. One method of increasing the overall rate of the reaction is to decrease the concentration of 3,3'-DMBP in the feed. As shown in FIG. 9, under otherwise identical conditions (10 wt % total DMBP, 150° C., and 1340 ppmW Co), oxidizing feeds having a very high concentration of 4-position methyl groups allows the reaction to proceed at higher rates.

The overall yield of M-Acid increases when 3,4'-DMBP and 4,4'-DMBP are very high in concentration in the feed. As shown in the table below, at otherwise similar conditions, (10 wt % total DMBP, 150° C., and 1340 ppmW Co) when the feed composition has very little 3,3'-DMBP and the process is run at similar conversion, the loss of product to the undesirable over-oxidized Acet-Acid, Aid-Acid and Di-Acid products is decreased from 2% to 0.5%, as demonstrated in Table 3 below.

TABLE 3

| Relative wt % in feed | | | Total Product Yields | | | | | | | | |
|---|---|---|---|---|---|---|---|---|---|---|---|
| 3,3'-DMBP | 3,4'-DMBP | 4,4'-DMBP | M-Alc | M-Ald | M-Acid | M-Acet | Acet-Acid | Ald-Acid | Di-Acid | % Conv | Total Over-oxidized |
| 56.1 | 33.9 | 10.0 | 0.5% | 10.4% | 33.3% | 2.4% | 0.1% | 1.1% | 0.8% | 50.0% | 2.0% |
| 0.8 | 73.1 | 26.1 | 2.0% | 24.5% | 20.4% | 2.6% | 0.0% | 0.4% | 0.1% | 50.0% | 0.5% |

The final yield of M-Acid from the 3,4'-DMBP and 4,4'-DMBP isomers increases when more 3,3'-DMBP is present in the feed. The data tables below, Tables 4 and 5, shows that when similar conversions of the individual isomers are compared, for example in Table 4, 82.6% and 84.4% conversion occurred in the two different experiments, the yield of undesirable over-oxidized Acet-Acid, Ald-Acid and Di-Acid products increased from 2.7 to 4.5% when the 3,3'-DMBP was not present in the feed.

TABLE 4

| Relative wt % in feed | | | Yield of 3,4'-isomers | | | | | | | | |
|---|---|---|---|---|---|---|---|---|---|---|---|
| 3,3'-DMBP | 3,4'-DMBP | 4,4'-DMBP | M-Alc | M-Ald | M-Acid | M-Acet | Acet-Acid | Ald-Acid | Di-Acid | % Conv | Total Over-oxidized |
| 56.1 | 33.9 | 10.0 | 0.7% | 17.5% | 54.8% | 3.8% | 0.1% | 1.6% | 0.97% | 82.6% | 2.7% |
| 0.8 | 73.1 | 26.1 | 0.8% | 22.8% | 55.4% | 3.2% | 0.3% | 2.4% | 1.8% | 84.4% | 4.5% |

TABLE 5

| Relative wt % in feed | | | Yield of 4,4'-isomers | | | | | | | | |
|---|---|---|---|---|---|---|---|---|---|---|---|
| 3,3'-DMBP | 3,4'-DMBP | 4,4'-DMBP | M-Alc | M-Ald | M-Acid | M-Acet | Acet-Acid | Ald-Acid | Di-Acid | % Conv | Total Over-oxidized |
| 56.1 | 33.9 | 10.0 | 0.4% | 8.0% | 69.5% | 2.2% | 0.7% | 3.8% | 1.4% | 99.6% | 5.9% |
| 0.8 | 73.1 | 26.1 | 0.1% | 10.6% | 70.0% | 1.8% | 1.6% | 6.3% | 4.6% | 99.5% | 12.5% |

Example 6

Effects of Varying Water Concentrations on DMBP Oxidation

The oxidation process is sensitive to various concentrations of water. The process can proceed efficiently with up to 10 wt % of water without significant changes in selectivity or kinetics. Table 6 below shows that the fitted rate constants for the individual isomers of DMBP during an oxidation of a mixture of DMBP isomers decrease when water is added. This hindering of the reaction rate benefits the reaction selectivity by decreasing the yield of undesired over-oxidation by-products, Ald-Acid and Di-Acid, shown in Table 7. Other intermediates such as M-Acet and M-Alc also increase in yield, however, they can ultimately be converted to the desired M-Acid product by recycle to the oxidation reaction.

TABLE 6

| | $1^{ST}$ Order Rate Constants ($s^{-1}$) | | |
|---|---|---|---|
| Conditions | 3,3'-DMBP | 3,4'-DMBP | 4,4'-DMBP |
| No added $H_2O$ | 5.4E−05 | 3.9E−04 | 1.4E−03 |
| 5 wt % $H_2O$ | 3.9E−05 | 2.7E−04 | 1.0E−03 |
| 10 wt % $H_2O$ | 2.3E−05 | 1.3E−04 | 4.3E−04 |

TABLE 7

| | Yields of DMBP products | | | | | | | | |
|---|---|---|---|---|---|---|---|---|---|
| Conditions | M-Alc | M-Ald | M-Acid | M-Acet | Acet-Acid | Ald-Acid | Di-Acid | Total Over-Oxidized | % Conv |
| No added $H_2O$ | 0.6% | 12.7% | 24.9% | 2.2% | 0.0% | 0.66% | 0.19% | 0.86% | 42.0% |
| 5 wt % $H_2O$ | 1.0% | 12.7% | 22.7% | 3.8% | 0.0% | 0.58% | 0.14% | 0.71% | 42.0% |
| 10 wt % $H_2O$ | 1.5% | 10.0% | 22.9% | 5.2% | 0.0% | 0.18% | 0.09% | 0.27% | 42.0% |

Example 7

Manipulation of Solid-Liquid Equilibrium to Reduce Over-Oxidation

Melting point data for several DMBP isomers and the corresponding oxidation products are displayed in Table 8. The data in this table show that within each family of isomers, the melting point (which correlates inversely with solubility) increases with the degree of oxidation. This data indicates that for each isomer family, the molecule will become less soluble as it is oxidized from an aldehyde to a mono-acid and eventually to a di-acid. FIG. 4 confirms this conclusion showing that the DiAcid products have a higher disolution temperature than mono-acid products of the same isomer family.

TABLE 8

| Chemical Name | Melting Temperature (° C.) |
| --- | --- |
| 4'-methyl-[1,1'-biphenyl]-3-carbaldehyde | 12.5 |
| 3'-methyl-[1,1'-biphenyl]-4-carbaldehyde | 47.0 |
| 4'-methyl-[1,1'-biphenyl]-4-carbaldehyde | 105.9 |
| 4,4'-dimethyl-[1,1'-biphenyl] | 121.4 |
| 3'-methyl-[1,1'-biphenyl]-3-carboxylic acid | 133.7 |
| 2'-methyl-[1,1'-biphenyl]-3-carboxylic acid | 141.3 |
| 3'-Formyl-[1,1'-biphenyl]-3-carboxylic acid | 185.0 |
| 4'-methyl-[1,1'-biphenyl]-3-carboxylic acid | 185.5 |
| 2'-methyl-[1,1'-biphenyl]-4-carboxylic acid | 189.5 |
| 4'-Formyl-[1,1'-biphenyl]-3-carboxylic acid | 193.9 |
| 3'-methyl-[1,1'-biphenyl]-4-carboxylic acid | 203.0 |
| 3'-Formyl-[1,1'-biphenyl]-4-carboxylic acid | 247.8 |
| 4'-methyl-[1,1'-biphenyl]-4-carboxylic acid | 254.5 |
| 4'-Formyl-[1,1'-biphenyl]-4-carboxylic acid | >300 |
| 3,3'-dicarboxylic acid-[1,1'-biphenyl] | >330 |
| 3,4'-dicarboxylic acid-[1,1'-biphenyl] | >330 |
| 4,4'-dicarboxylic acid-[1,1'-biphenyl] | >330 |

FIG. 4 also shows that at the standard target temperature (150° C.) all of the M-acid would be soluble in reactions of typical concentrations. It is clear from this diagram, that reactor conditions could be chosen such that a starting DMBP solution would be completely soluble in acetic acid, but oxidation products would precipitate. Higher DMBP concentration, lower temperature or removal of solvent all favor the precipitation of oxidation products. In this example, the reactor temperature is reduced to 40° C. and the individual weight percent of 3,3'-DMBP, 3,4'-DMBP, 4,3'-DMBP, 4,4'-DMBP is increased to 8% (32 wt % overall DMBP) in order to facilitate the precipitation of the 3,4', 4,3' and 4,4' mono-acid isomers at higher conversion. Precipitation of these mono-acid isomers will prevent further oxidation of these molecules and reduce selectivity to over-oxidation products.

Example 8

Oxidation of Mixed DMBP Isomers (3,3'-, 3,4'-, and 4,4'-DMBP) with Other Metals A 300 ml Parr reactor was charged with 15 grams of a dimethylbiphenyl mixed isomer feed (with the following composition 25 wt % 3,3'-DMBP, 55 wt % 3,4'-DMBP, and 20 wt % 4,4'-DMBP), and 135 gms acetic acid. The type of metal acetate and its concentration that was added for each experiment is give in Table 9 below. The reactor was sealed and pressurized to 500 psig (3549 kPa-a) with nitrogen. The reactor was heated to 150° C. with a stir rate of 1200 rpm under 1500 cc/min $N_2$. When the temperature reached 150° C., $N_2$ was switched to air at the same flow rate. During the reaction, liquid samples were taken for GC analysis and the oxygen concentration in the gas effluent was measured. After the reaction, the air flow was switched to $N_2$, the reactor was cooled to room temperature then depressurized. The yields are shown in Table 9 for comparison. The various metals or metal combinations shown were all able to successfully catalyze the oxidation of DMBP.

TABLE 9

| Total Metals (mM) | Metal Acetates (relative mol %) | Product Yields | | | | | | |
| --- | --- | --- | --- | --- | --- | --- | --- | --- |
| | | M-Alc | M-Ald | M-Acid | M-Acet | Ald-Acid | Di-Acid | Conv % |
| 15.1 | 90% Co(II):10% Mn(II) | 0.7% | 13.2% | 26.4% | 6.2% | 0.9% | 0.3% | 50.0% |
| 30.2 | 100% Mn(II) | 0.5% | 7.8% | 27.1% | 8.2% | 0.9% | 1.9% | 50.0% |
| 15.1 | 50% Co(II):50% Ni(II) | 1.5% | 14.0% | 24.5% | 5.5% | 0.6% | 0.4% | 50.0% |
| 15.1 | 50% Co(II):50% Zn(II) | 1.4% | 13.5% | 24.7% | 6.2% | 0.7% | 0.4% | 50.0% |
| 15.1 | 50% Co(II):50% Zr(II) | 1.3% | 16.3% | 25.2% | 2.4% | 0.9% | 0.6% | 50.0% |
| 15.1 | 50% Co(II):50% Fe(II) | 1.5% | 12.1% | 16.6% | 6.6% | 0.2% | 0.1% | 39.0% |

Example 9

Comparison of Oxidation of DMBP Isomers with Varying Reaction Temperatures

The overall yield of the reaction can be increased by decreasing the temperature of the reaction. Table 10 compares data from single-pass experiments that only vary from each other in temperature (20 wt % total DMBP and 23 mM Co). The yield of undesirable overoxidized, Acet-Acid, Ald-Acid and Di-Acid, products is smaller at lower temperatures; at 130° C., the yield loss through formation of these over-oxidized products is 23% less (2.0% compared to 2.6%) than at 150° C. The final process with isolated M-Acid and recycled under-oxidized products will have a much lower yield loss if operated at a lower temperature.

TABLE 10

| | | | | Total Product Yields | | | | |
|---|---|---|---|---|---|---|---|---|
| Temp (° C.) | M-Alc | M-Ald | M-Acid | M-Acet | Acet-Acid | Ald-Acid | Di-Acid | % Conv | Total Over-oxidized |
| 130 | 0.8% | 6.4% | 34.6% | 3.1% | 0.2% | 0.8% | 1.0% | 50.0% | 2.0% |
| 150 | 0.9% | 8.4% | 32.7% | 2.1% | 0.2% | 1.0% | 1.4% | 50.0% | 2.6% |

Another example showed that there is a an additional increase in the mono-acid/mono-aldehyde ratio as temperature is decreased to 110° C. Oxidizing pure 4,4'-DMBP at 150° C., 130° C., and 110° C. the M-Acid/M-Ald ratio increased from 0.76 to 1.0, as demonstrated in Table 11.

TABLE 11

| | | | Total Product Yields | | | | | |
|---|---|---|---|---|---|---|---|---|---|
| Temp (° C.) | M-Alc | M-Ald | M-Acid | M-Acet | Ald-Acid | Di-Acid | % Conv | Total Over-oxidized | M-Acid/M-Ald |
| 150 | 3.29% | 22.73% | 17.34% | 10.36% | 1.38% | 0.49% | 60% | 1.86% | 0.76 |
| 130 | 5.68% | 23.14% | 19.26% | 3.53% | 0.77% | 0.00% | 60% | 0.77% | 0.83 |
| 110 | 3.07% | 22.81% | 22.74% | 4.94% | 1.11% | 0.00% | 60% | 1.11% | 1.00 |

Figure 10:
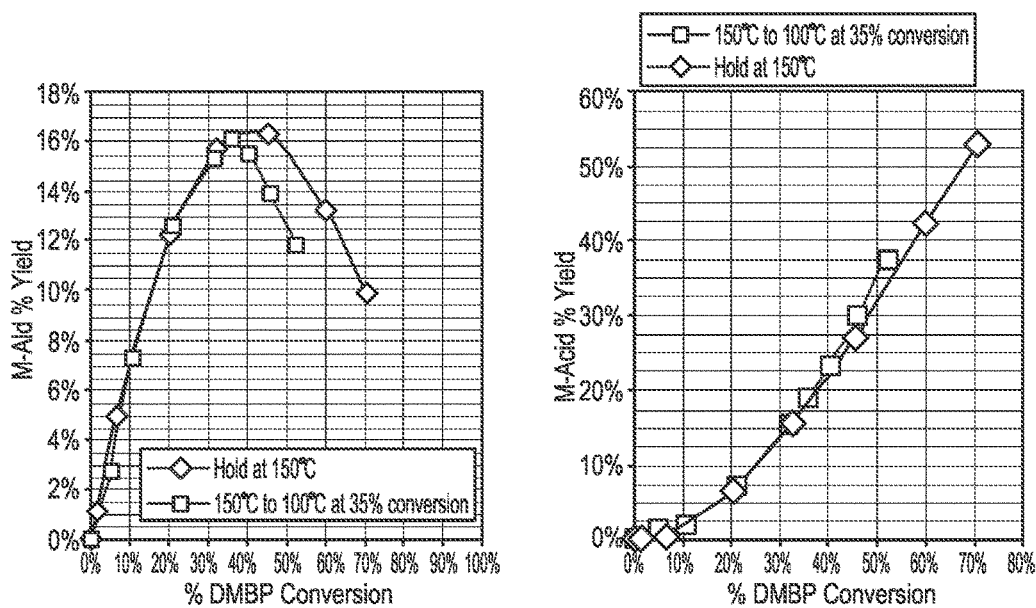
FIG. 10 demonstrates the advantages of a two-step temperature oxidation of DMBP to M-Ald relative to M-Acid.

M-Ald can be oxidized more efficiently at low temperature compared to M-Acid. A two-step reaction where the reaction is initiated at a higher temperature and reduced to a lower temperature reduces the M-Ald yield and increases M-Acid yield. In addition to increasing the M-Acid yield directly, the reduced M-Ald yield makes it easier to purify and isolate the desired M-Acids. As shown in FIG. 10, compared to holding the temperature at 150° C. for the entire reaction, dropping the temperature to 100° C. at 35% conversion allow the yields at 50% conversion to change in a beneficial way: the M-Ald yield decreased from 15.5% to 12.5%, while the M-Acid yield increased from 32 to 35%.

Example 10

Effects of Various Initiators on DMBP Oxidation

Figure 11:
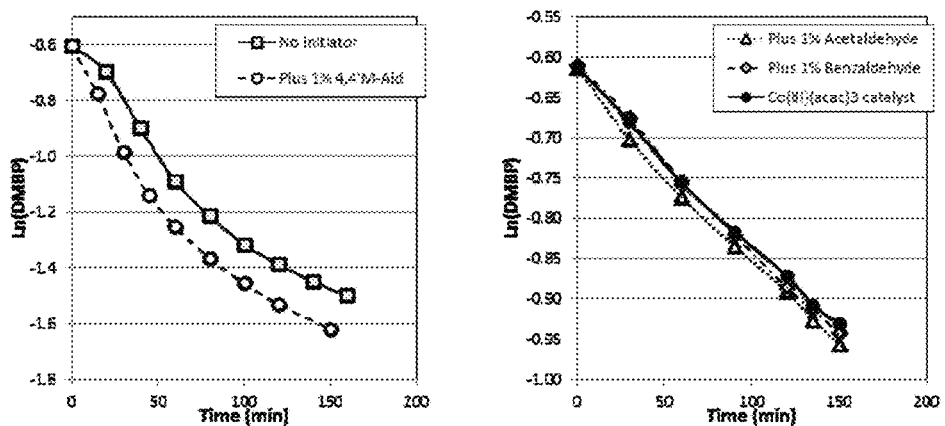
FIG. 11 demonstrates the effects of utilizing various initiators for the oxidation of DMBP.

The reaction can be initiated using Co(III)(acetylacetonate)$_3$ (Cobalt AcAc) or aldehydes such as benzaldehyde, acetaldehyde, or M-Ald intermediates. The initiation allows the reaction to proceed at time zero at close to the steady state rate observed in reactions without initiators. M-Ald will be present in the under-oxidized products that can be recycled back to the feed and can thus act as an initiators in the process. In FIG. 11 below, 4,4'-M-Ald can be seen as an initiator in the oxidation of a mixed isomer DMBP feed (23 mM Co and 150° C.). The non-initiated reaction takes about 35 minutes to reach the maximum reaction rate that is observed almost immediately in the initiated reaction. On the right, oxidation of 10 wt % of the pure 3,3'-DMBP isomer at 150° C. with 15 mM Co takes days before autoxidation and reaction initiation occurs. Under the same conditions with added initiators, such as Co(III)(acetylacetonate)$_3$ (as the source of Co) or aldehydes such as benzaldehyde and acetaldehyde, this isomer can be oxidized without delay.

Example 11

Effects of Varying Catalyst Concentrations on DMBP Oxidation

Figure 12:
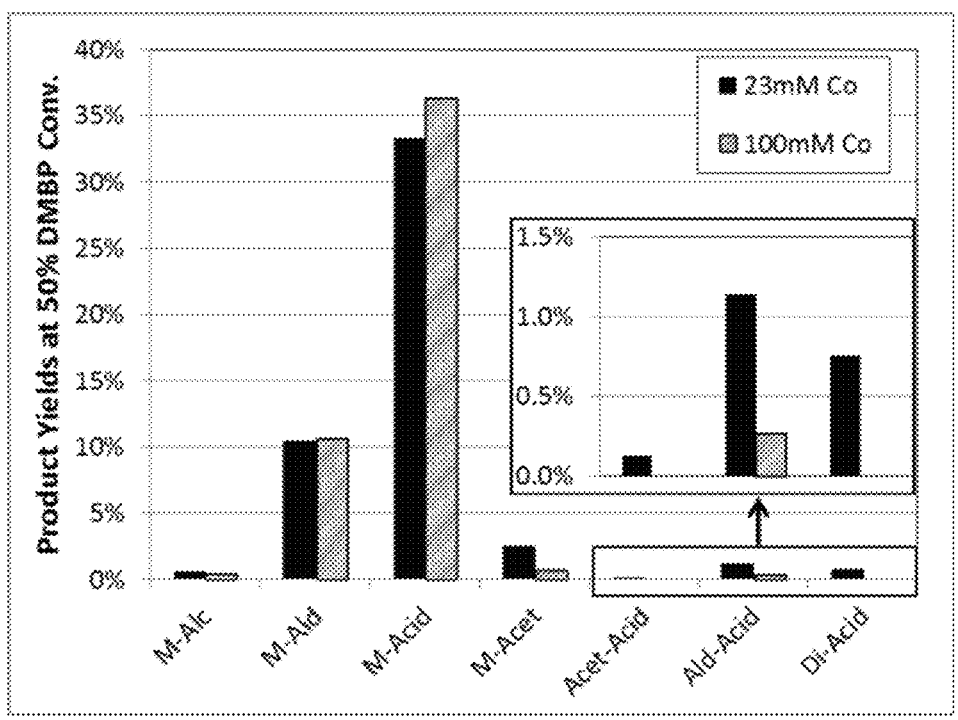
FIG. 12 demonstrates the changes in product yields as a result of different catalyst concentrations.

Very high catalyst concentrations can be used to achieve increased M-Acid yield and decrease side-reactions that produced undesired by-products and over-oxidation products. This could be caused by an increase in rate of cobalt catalyzed reactions relative to radical C—H bond attack, which is more strongly oxidizing. The reaction can benefit from higher concentrations of all catalysts that initiate the radical reaction by oxidation of DMBP. FIG. 12 shows the increase in selectivity of M-Acid and decrease in selectivity of M-Alc, M-Acet, Acet-Acid, Ald-Acid, and Di-Acid that results from the increase in catalyst concentration from 23 mM to 100 mM.

Comparative Example

Oxidation of Mixed DMBP Isomers (3,3'-, 3,4'-, and 4,4'-DMBP) with Co/Mn/Br$_2$ A 300 ml Parr reactor was charged with 15 grams of a dimethylbiphenyl mixed isomer feed (with the following composition 56 wt % 3,3'-DMBP, 34 wt % 3,4'-DMBP, and 10 wt % 4,4'-DMBP), and 135 gms acetic acid. CoBr$_2$ and MnBr$_2$ were added to a concentration of 11.4 mM each. The reactor was sealed and pressurized to 500 psig (3549 kPa-a) with nitrogen. The reactor was heated to 100° C. with a stir rate of 1200 rpm under 1500 cc/min N$_2$. When the temperature reached 100° C., N$_2$ was switched to air at the same flow rate. During the reaction, liquid samples were taken for GC analysis and the oxygen concentration in the gas effluent was measured. After the reaction, the air flow was switched to N$_2$, the reactor was cooled to room temperature then depressurized. The yields were interpolated to 50%, conversion and are shown in Table 12. Compared to the other conditions, especially from experiments performed closer to 100° C., bromide-containing catalysts do not provide selectivity to M-Acids.

TABLE 12

| | Yields at 50% conversion of DMBP | | | | | | |
|---|---|---|---|---|---|---|---|
| Catalyst | M-Alc | M-Ald | M-Acid | M-Acet | Ald-Acid | Di-Acid | Conv % |
| CoBr$_2$:MnBr$_2$ 11.4 mM each | 4.9% | 20.8% | 13.7% | 0.4% | 1.8% | 0.5% | 50.0% |

Further illustrative, non-exclusive examples of systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action. PCT/EP Clauses:

1. A process for selective oxidation of dimethyl-1,1'-biphenyl(s) to form methyl-1,1'-biphenyl mono-carboxylic acid(s), comprising contacting a solution of dimethyl-1,1'-biphenyl(s) in acetic acid in the presence of an oxidation catalyst and air under time and temperature conditions sufficient to oxidize the dimethyl-1,1'-biphenyl(s) into one or more methyl-1,1'-biphenyl mono-carboxylic acid(s) products, conducting at least one of (i) adding an antisolvent, or (ii) optimizing a total conversion of dimethyl-1,1'-biphenyl(s) by oxidation based upon a molar ratio of dimethyl-1,1'-biphenyl isomers, or (iii) precipitating the methyl-1,1'-biphenyl mono-carboxylic acid(s) products by lowering the temperature, or (iv) decreasing the oxidation reaction temperature to enhance conversion of aldehydes over methyl functional groups, so as to limit over-oxidation of the dimethyl-1,1'-biphenyl(s), wherein the oxidation reaction is conducted in the absence of bromide-containing catalysts.

2. The process of paragraph PCT1, wherein the catalyst is Mn(II) acetate or Co(II) acetate or combinations of Co(II) acetate and other metal acetate catalysts.

3. The process of paragraph PCT1 or PCT2, wherein the selectivity for formation of methyl-1,1'-biphenyl mono-carboxylic acids is enhanced relative to the formation of other 1,1'-biphenyl oxygenates.

4. The process of any of paragraphs PCT1 to PCT3, wherein the process comprises adding water as the antisolvent.

5. The process of any of paragraphs PCT1 to PCT4, wherein the dimethyl-1,1'-biphenyl is provided in a mixture of dimethylbiphenyl isomers.

6. The process of any of paragraphs PCT1 to PCT5, further comprising separating 2,3'- and 2,4'-isomers of dimethylbiphenyl from 3,3'-dimethylbiphenyl, 3,4'-dimethylbiphenyl and 4,4'-dimethylbiphenyl by distillation, and dissolving the 3,3'-, 3,4'- and 4,4'-isomers of dimethylbiphenyl in the acetic acid to form the solution.

7. The process of any of paragraphs PCT1 to PCT6, further comprising limiting the total conversion to 55-70% when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates; or limiting the total conversion to 45-55% when the 3,3'-isomers of dimethylbiphenyl comprise between 10 and 30 wt % in the feed, so as to increase the overall yield of methyl-1,1'-biphenyl mono-carboxylic acids relative to other 1,1'-biphenyl oxygenates; or limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

8. The process of any of paragraphs PCT1 to PCT7, wherein precipitation of the methyl-1,1'-biphenyl mono-carboxylic acid(s) products is achieved by removing solvent.

9. The process of any of paragraphs PCT1 to PCT7, wherein precipitation of the methyl-1,1'-biphenyl mono-carboxylic acid(s) products is achieved by optimizing the oxidation reaction temperature and solute concentrations of the methyl-1,1'-biphenyl mono-carboxylic acid(s), to cause precipitation of the methyl-1,1'-biphenyl mono-carboxylic acid(s) products prior to over-oxidation, such as wherein the oxidation reaction temperature is reduced from an oxidation initiation temperature to from 40° C. to less than 60° C., or even wherein the oxidation reaction temperature is 50° C., and the solute concentration of methyl-1,1'-biphenyl mono-carboxylic acid(s) products is above 2 wt %, such as wherein the solute concentration of methyl-1,1'-biphenyl mono-carboxylic acid(s) products is from 2 wt % to 10 wt %.

10. The process of any of paragraphs PCT1 to PCT9, wherein the oxidation reaction temperature is controlled to be from 100° C. to 150° C., or even from 110° C. to 150° C., or even from 110° C. to 130° C., or wherein the oxidation reaction temperature starts at greater than or equal to 130° C. and is reduced to 100° C. after reaction initiation.

11. The process of any of paragraphs PCT1 to PCT10, wherein the catalyst is Co(II) acetate and further comprising adding one of Mn(II) acetate, Ni(II) acetate, Zn(II) acetate, Zr(IV) acetate, Fe(II) acetate or combinations thereof as the additional metal acetate catalyst, which catalysts can be present in concentrations in the solution from 7.6 mM (450 ppm) to 100 mM (6000 ppm), or from 23 mM (1350 ppm) to 100 mM (6000 ppm).

12. The process of any of paragraphs PCT1 to PCT11, wherein the process further comprises adding Co(III)(acetylacetonate)$_3$, benzaldehyde, acetaldehyde or biphenyl-aldehydes as an initiator.

13. The process of any of paragraphs PCT1 to PCT12, further comprising separation of the methyl-1,1'-biphenyl mono-carboxylic acid(s) products from under-oxidized intermediates and over-oxidized products, and recycling the under-oxidized intermediates to the oxidation process.

14. The process of any of paragraphs PCT1 to PCT13, wherein the methyl-1,1'-biphenyl mono-carboxylic acids products formed are one or more of 3,3'-methyl-1,1'-biphenyl mono-carboxylic acid, 3,4'-methyl-1,1'-biphenyl mono-carboxylic acid, 4,3'-methyl-1,1'-biphenyl mono-carboxylic acid, and 4,4'-methyl-1,1'-biphenyl mono-carboxylic acid.

15. A process for forming methylbiphenyl mono-esters comprising selectively oxidizing dimethyl-1,1'-biphenyl(s) to form methyl-1,1'-biphenyl mono-carboxylic acid(s), according to any of paragraphs PCT1 to PCT14, and further reacting the methyl-1,1'-biphenyl mono-carboxylic acid(s) products with $C_4$ to $C_{13}$ alcohols, preferably OXO-alcohols, under esterification conditions.

INDUSTRIAL APPLICABILITY

The systems and methods disclosed herein are applicable to the chemical industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A process for selective oxidation of dimethyl-1,1'-biphenyl(s) to form methyl-1,1'-biphenyl mono-carboxylic acid(s), comprising:
   providing a mixture of dimethylbiphenyl isomers;
   separating 2,3'- and 2,4'-isomers of dimethylbiphenyl in the mixture from 3,3'-, 3,4'-, and 4,4'-isomers of dimethylbiphenyl by distillation, and then dissolving the 3,3'-, 3,4'- and 4,4'-isomers of dimethylbiphenyl in acetic acid to form a solution;
   contacting the solution with an oxidation catalyst and air under time and temperature conditions sufficient to oxidize the dimethyl-1,1'-biphenyl(s) into one or more methyl-1,1'-biphenyl mono-carboxylic acid(s) products;
   conducting at least one of:
   (i) adding an antisolvent, or
   (ii) optimizing a total conversion of dimethyl-1,1'-biphenyl(s) by oxidation based upon a molar ratio of dimethyl-1,1'-biphenyl isomers, or
   (iii) precipitating the methyl-1,1'-biphenyl mono-carboxylic acid(s) products by lowering the temperature, or
   (iv) decreasing the oxidation reaction temperature to enhance conversion of aldehydes over methyl functional groups,
   so as to limit over-oxidation of the dimethyl-1,1'-biphenyl(s),
   wherein the oxidation reaction is conducted in the absence of bromide-containing catalysts, and
   wherein the total conversion is limited to 55-70% when the 3,3'-isomers of dimethylbiphenyl comprise less than 10 wt % of the solution, so as to increase the overall yield of methyl-1,1'-biphenyl mono-carboxylic acids relative to other 1,1'-biphenyl oxygenates.

2. The process of claim 1, wherein the catalyst is Mn(II) acetate or Co(II) acetate or combinations of Co(II) acetate and other metal acetate catalysts.

3. The process of claim 1, comprising adding water as the antisolvent.

4. The process of claim 1, further comprising limiting the total conversion to 45-55% when the 3,3'-isomers of dimethylbiphenyl comprise between 10 and 30 wt % in the feed, so as to increase the overall yield of methyl-1,1'-biphenyl mono-carboxylic acids relative to other 1,1'-biphenyl oxygenates.

5. The process of claim 1, further comprising limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

6. The process of claim 1, wherein precipitation of the methyl-1,1'-biphenyl mono-carboxylic acid(s) products is achieved by removing solvent.

7. The process of claim 1, wherein precipitation of the methyl-1,1'-biphenyl mono-carboxylic acid(s) products is achieved by optimizing the oxidation reaction temperature and solute concentrations of the methyl-1,1'-biphenyl mono-carboxylic acid(s), to cause precipitation of the methyl-1,1'-biphenyl mono-carboxylic acid(s) products prior to over-oxidation.

8. The process of claim 7, wherein the oxidation reaction temperature is reduced from an oxidation initiation temperature to from about 40° C. to less than about 60° C.

9. The process of claim 7, wherein the solute concentration of methyl-1,1'-biphenyl mono-carboxylic acid(s) products is above about 2 wt %.

10. The process of claim 1, wherein the oxidation reaction temperature is controlled to be from about 100° C. to about 150° C.

11. The process of claim 10, wherein the oxidation reaction temperature is controlled to be from about 110° C. to about 150° C.

12. The process of claim 10, wherein the oxidation reaction temperature is controlled to be from about 110° C. to about 130° C.

13. The process of claim 10, wherein the oxidation reaction temperature starts at greater than or equal to about 130° C. and is reduced to about 100° C. after reaction initiation.

14. The process of claim 1, wherein the catalyst is Co(II) acetate and further comprising adding one of Mn(II) acetate, Ni(II) acetate, Zn(II) acetate, Zr(IV) acetate, Fe(II) acetate or combinations thereof as the additional metal acetate catalyst.

15. The process of claim 1, further comprising adding Co(III)(acetylacetonate)$_3$, benzaldehyde, acetaldehyde or recycling intermediate methyl-biphenyl-aldehydes as an initiator.

16. The process of claim 1, wherein the catalyst concentration in the solution is from about 7.6 mM (450 ppm) to about 100 mM (6000 ppm).

17. The process of claim 15, wherein the catalyst concentration in the solution is from about 23 mM (1350 ppm) to about 100 mM (6000 ppm).

18. The process of claim 1, further comprising separation of the methyl-1,1'-biphenyl mono-carboxylic acid(s) products from under-oxidized intermediates and over-oxidized products, and recycling the under-oxidized intermediates to the oxidation process.

19. The process of claim 1, wherein the methyl-1,1'-biphenyl mono-carboxylic acids products formed are one or more of 3,3'-methyl-1,1'-biphenyl mono-carboxylic acid, 3,4'-methyl-1,1'-biphenyl mono-carboxylic acid, 4,3'-methyl-1,1'-biphenyl mono-carboxylic acid, and 4,4'-methyl-1,1'-biphenyl mono-carboxylic acid.

20. A process for forming methylbiphenyl mono-esters, comprising:
   providing a mixture of dimethylbiphenyl isomers;
   separating 2,3'- and 2,4'-isomers of dimethylbiphenyl in the mixture from 3,3'-, 3,4'-, and 4,4'-isomers of dimethylbiphenyl by distillation, and then dissolving the 3,3'-, 3,4'- and 4,4'-isomers of dimethylbiphenyl in acetic acid to form a solution;
   selectively oxidizing the dimethyl-1,1'-biphenyl(s) to form methyl-1,1'-biphenyl mono-carboxylic acid(s), by contacting the solution with an oxidation catalyst and air under time and temperature conditions sufficient to oxidize the dimethyl-1,1'-biphenyl(s) into one or more methyl-1,1'-biphenyl mono-carboxylic acid(s) products;

conducting at least one of:
(i) adding an antisolvent, or
(ii) optimizing a total conversion of dimethyl-1,1'-biphenyl(s) by oxidation based upon a molar ratio of dimethyl-1,1'-biphenyl isomers, or
(iii) precipitating the methyl-1,1'-biphenyl mono-carboxylic acid(s) products, or
(iv) optimizing the oxidation reaction temperature, so as to limit over-oxidation of the dimethyl-1,1'-biphenyl(s);
wherein the oxidation reaction is conducted in the absence of bromide-containing catalysts; and
wherein the total conversion is limited to 45-55% when the 3,3'-isomers of dimethylbiphenyl comprise between 10 and 30 wt % of the solution, so as to increase the overall yield of methyl-1,1'-biphenyl mono-carboxylic acids relative to other 1,1'-biphenyl oxygenates;
further reacting the methyl-1,1'-biphenyl mono-carboxylic acid(s) products with $C_4$ to $C_{13}$ alcohols under esterification conditions.

21. The process of claim 20, wherein the catalyst is Mn(II) acetate or Co(II) acetate or combinations of Co(II) acetate and other metal acetate catalysts.

22. The process of claim 20, comprising adding water as the antisolvent.

23. The process of claim 20, further comprising limiting the total conversion to 55-70% when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates.

24. The process of claim 20, further comprising limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

25. The process of claim 20, wherein precipitation of the methyl-1,1'-biphenyl mono-carboxylic acid(s) products is achieved by removing solvent.

26. The process of claim 20, wherein precipitation of the methyl-1,1'-biphenyl mono-carboxylic acid(s) products is achieved by optimizing the oxidation reaction temperature and solute concentrations of the methyl-1,1'-biphenyl mono-carboxylic acid(s), to cause precipitation of the methyl-1,1'-biphenyl mono-carboxylic acid(s) products prior to over-oxidation.

27. The process of claim 26, wherein the oxidation reaction temperature is reduced from an oxidation initiation temperature to from about 40° C. to less than about 60° C.

28. The process of claim 26, wherein the solute concentration of methyl-1,1'-biphenyl mono-carboxylic acid(s) products is above about 2 wt %.

29. The process of claim 20, wherein the oxidation reaction temperature is controlled to be from about 100° C. to about 150° C.

30. The process of claim 29, wherein the oxidation reaction temperature is controlled to be from about 110° C. to about 150° C.

31. The process of claim 30, wherein the oxidation reaction temperature is controlled to be from about 110° C. to about 130° C.

32. The process of claim 29, wherein the oxidation reaction temperature starts at greater than or equal to about 130° C. and is reduced to about 100° C. after reaction initiation.

33. The process of claim 20, wherein the catalyst is Co(II) acetate and further comprising adding one of Mn(II) acetate, Ni(II) acetate, Zn(II) acetate, Zr(IV) acetate, Fe(II) acetate or combinations thereof as the additional metal acetate catalyst.

34. The process of claim 20, further comprising adding Co(III)(acetylacetonate)$_3$, benzaldehyde, acetaldehyde or biphenyl-aldehydes as an initiator.

35. The process of claim 20, wherein the catalyst concentration in the solution is from about 7.6 mM (450 ppm) to about 100 mM (6000 ppm).

36. The process of claim 35, wherein the catalyst concentration in the solution is from about 23 mM (1350 ppm) to about 100 mM (6000 ppm).

37. The process of claim 20, further comprising separation of the methyl-1,1'-biphenyl mono-carboxylic acid(s) products from under-oxidized intermediates and over-oxidized products, and recycling the under-oxidized intermediates to the oxidation process.

38. The process of claim 20, wherein the methyl-1,1'-biphenyl mono-carboxylic acids products formed are one or more of 3,3'-methyl-1,1'-biphenyl mono-carboxylic acid, 3,4'-methyl-1,1'-biphenyl mono-carboxylic acid, 4,3'-methyl-1,1'-biphenyl mono-carboxylic acid, and 4,4'-methyl-1,1'-biphenyl mono-carboxylic acid.

39. The process of claim 20, wherein the alcohols are OXO-alcohols.

40. A process for selective oxidation of dimethyl-1,1'-biphenyl(s) to form methyl-1,1'-biphenyl mono-carboxylic acid(s), comprising:
providing a mixture of dimethylbiphenyl isomers;
separating 2,3'- and 2,4'-isomers of dimethylbiphenyl in the mixture from 3,3'-, 3,4'-, and 4,4'-isomers of dimethylbiphenyl by distillation, and then dissolving the 3,3'-, 3,4'- and 4,4'-isomers of dimethylbiphenyl in acetic acid to form a solution;
contacting the solution with an oxidation catalyst and air under time and temperature conditions sufficient to oxidize the dimethyl-1,1'-biphenyl(s) into one or more methyl-1,1'-biphenyl mono-carboxylic acid(s) products;
conducting at least one of:
(i) adding an antisolvent, or
(ii) optimizing a total conversion of dimethyl-1,1'-biphenyl(s) by oxidation based upon a molar ratio of dimethyl-1,1'-biphenyl isomers, or
(iii) precipitating the methyl-1,1'-biphenyl mono-carboxylic acid(s) products by lowering the temperature, or
(iv) decreasing the oxidation reaction temperature to enhance conversion of aldehydes over methyl functional groups,
so as to limit over-oxidation of the dimethyl-1,1'-biphenyl(s),
wherein the oxidation reaction is conducted in the absence of bromide-containing catalysts, and
wherein the total conversion is limited to 30-45% when the 3,3'-isomers of dimethylbiphenyl comprise between 30 and 80 wt % of the solution, so as to increase the overall yield of methyl-1,1'-biphenyl mono-carboxylic acids relative to other 1,1'-biphenyl oxygenates.

* * * * *